US007896256B2

(12) United States Patent
Robbinis-Sullivan et al.

(10) Patent No.: US 7,896,256 B2
(45) Date of Patent: Mar. 1, 2011

(54) DISPOSABLE PIERCED EARRING FRAGRANCE CHAMBER

(75) Inventors: Kathryn S. Robbinis-Sullivan, San Marino, CA (US); Mark A. Calkins, San Jacinto, CA (US)

(73) Assignee: Kathryn S. Robbins-Sullivan, San Marino, CA (US)

(*) Notice: Subject to any disclaimer, the term of this patent is extended or adjusted under 35 U.S.C. 154(b) by 135 days.

(21) Appl. No.: 12/255,387

(22) Filed: Oct. 21, 2008

(65) Prior Publication Data

US 2009/0260393 A1 Oct. 22, 2009

Related U.S. Application Data

(63) Continuation-in-part of application No. 11/328,598, filed on Jan. 11, 2006, now abandoned.

(51) Int. Cl.
*A24F 25/00* (2006.01)

(52) U.S. Cl. ........................................................ 239/36

(58) Field of Classification Search ................... 239/34, 239/36, 51.5, 57; 63/1.14, 1.15, DIG. 2
See application file for complete search history.

(56) References Cited

U.S. PATENT DOCUMENTS

| | | | |
|---|---|---|---|
| 130,421 | A | 8/1872 | Fredrick |
| 152,197 | A | 6/1874 | Wachter |
| 168,972 | A | 10/1875 | Dayton |
| 195,324 | A | 9/1877 | Atkinson |
| 292,963 | A | 2/1884 | Thie |
| 331,937 | A | 12/1885 | Birge |
| 367,976 | A | 8/1887 | Hartmann |
| 581,837 | A | 5/1897 | Walker |
| 1,257,848 | A | 2/1918 | Griffin |
| 1,625,375 | A | 3/1924 | Reyes |
| 1,574,962 | A | 2/1925 | Fischer |
| 1,673,617 | A | 3/1927 | Clark |
| 1,683,545 | A | 9/1928 | Harris |
| 1,899,165 | A | 2/1929 | Rivet |
| 2,079,043 | A | 5/1936 | Samstag |
| 2,194,379 | A | 9/1938 | Bicks |
| 2,234,062 | A | 5/1940 | Roberts |
| 2,471,949 | A | 4/1944 | Gilowicz |
| 2,620,227 | A | 11/1949 | Iwase |
| 2,751,764 | A | 4/1953 | Hudes |

(Continued)

OTHER PUBLICATIONS

Office Action for European Patent Application 06801932.2 dated Dec. 2, 2009, 5 pages.

(Continued)

*Primary Examiner*—Davis Hwu
(74) *Attorney, Agent, or Firm*—Jeffrey G. Sheldon; Sheldon Mak & Anderson

(57) ABSTRACT

A disposable fragrance chamber (10) for dispensing a fragrance from an aromatic liquid. The disposable fragrance chamber (10) consists of an outer casing body (20) having pad exposure openings (24), a detachable lid (34) and an absorbent pad (30) disposed between the body (20) and the lid (34). The chamber (10) permits an aromatic liquid to be applied into the absorbent pad (30) through the pad exposure openings (24). The aromatic liquid emits a fragrance into the surrounding environment when the chamber (10) is installed on an earring post (40) that extends beyond a person's ear lobe (48) held in place with an earring clasp (50).

24 Claims, 6 Drawing Sheets

U.S. PATENT DOCUMENTS

| | | | | |
|---|---|---|---|---|
| 2,922,963 | A | 1/1960 | Beatty | |
| 3,270,525 | A | 9/1966 | Sellers | |
| 3,605,437 | A | 9/1971 | Litton | |
| 3,828,577 | A | 8/1974 | Haynes | |
| 3,949,568 | A | 4/1976 | Gallagher | |
| 3,952,917 | A | 4/1976 | Gause | |
| 4,056,951 | A | 11/1977 | Black | |
| 4,159,631 | A | 7/1979 | Lee | |
| 4,241,850 | A | 12/1980 | Speer | |
| 4,315,570 | A * | 2/1982 | Silver et al. | 206/221 |
| 4,452,052 | A | 6/1984 | Hodge | |
| 4,712,389 | A | 12/1987 | Innis | |
| 4,785,642 | A | 11/1988 | Chin | |
| 5,031,419 | A | 7/1991 | Gelman | |
| 5,261,570 | A | 11/1993 | Hippely | |
| 5,316,182 | A | 5/1994 | Lee | |
| 5,390,510 | A | 2/1995 | Tirio-Cloonan | |
| 5,476,194 | A | 12/1995 | Hippely | |
| 6,357,260 | B1 | 3/2002 | Lutz | |
| 6,381,984 | B1 | 5/2002 | Russo | |
| 6,557,375 | B1 | 5/2003 | Simmons | |
| 6,662,596 | B2 | 12/2003 | Tsutsumi | |
| 6,675,613 | B2 | 1/2004 | Ashton | |
| 2002/0117556 | A1 | 8/2002 | Putz | |
| 2003/0061831 | A1 | 4/2003 | Tsutsumi | |
| 2004/0231360 | A1 | 11/2004 | Lagardere | |
| 2005/0034480 | A1 | 2/2005 | Martz | |

OTHER PUBLICATIONS

Supplementary European Search Report, EP 06801932, Jul. 9, 2009.
International Search Report, PCT US 06/32467, Aug. 10, 2007.

* cited by examiner

DISPOSABLE PIERCED EARRING FRAGRANCE CHAMBER

CROSS-REFERENCE

This application is a continuation-in-part of application Ser. No. 11/328,598, filed Jan. 11, 2006, now abandoned, which is incorporated herein by reference.

TECHNICAL FIELD

The invention generally pertains to fragrance dispensers, and more specifically to a disposable fragrance chamber that is worn by a person between a pierced earring and a earring clasp.

Currently, there are many types of jewelry dispensers for perfumes and medications that are available to provide a means for dispensing the fragrance of perfume over a period of time.

The prior art listed below did not disclose patents that possess any of the novelty of the instant invention; however the following U.S. patents are considered related: Inventor Issue Date U.S. Pat. No. 4,159,631 Lee Jul. 3, 1979 U.S. Pat. No. 4,353,370 Evans Oct. 12, 1982 U.S. Pat. No. 4,452,052 Hodge Jun. 5, 1984 U.S. Pat. No. 5,031,419 Gleman Jul. 16, 1981 U.S. Pat. No. 6,662,596 B2 Tsutsumi Dec. 16, 2003

Lee in U.S. Pat. No. 4,159,631 teaches a perfumed vapor dispensing article of jewelry in the shape of a hollow sphere having upper and lower halves secured together. A disc having gauze-filled cutouts is supported within the housing and wicks extend between sections of the gauze. Orifices in the upper half permit the perfumed vapors to escape. A hypodermic needle is inserted into the sphere's lower half to supply perfume.

In another embodiment the rod extends through the central aperture with removal of the rod permitting the lower half to be filled with an eyedropper.

U.S. Pat. No. 4,353,370 issued to Evans is for a medicated ear rod having a groove containing a cleaning agent and a stopper member utilizing a cotton saturated with alcohol or hydrogen peroxide that grasps the rod.

Hodge in U.S. Pat. No. 4,452,052 discloses an earring structure having an interior compartment which houses a removable perfume cartridge. The cartridge has a base containing the perfume, with a rotatable top having an aperture through which fragrance may escape. Rotation of the top piece changes the aperture area, thereby permitting the wearer to block the escape of fragrance.

Gleman in U.S. Pat. No. 5,031,419 teaches an earring clasp for pierced earrings which disposes a perfumed agent adjacent to or in contact with the person's ear lobe. The clasp is formed having a first and second disc member, and a body of sorbet material sandwiched in between the discs. A plurality of air holes permit air flow and in one embodiment the first disc is disposed adjacent to the person's ear lobe and is formed of a fluid pervious material to permit capillary transmission of the perfuming agent.

U.S. Pat. No. 6,662,596 B2 issued to Tsutsumi teaches a fragrance diffuser which covers the tip of the earring post to eliminate injury to the wearer. An outer case is mounted over the catch having an absorbent member with perfume impregnated therein. A number of openings in the outer case permit the fragrance to escape and a filling port permits the perfume such as the pipe from a spray nozzle to be inserted to impregnate the absorbent material.

For background purposes and as indicative of the art to which the invention is related reference may be made to the remaining cited patents issued to Wachter in U.S. Pat. No. 152,197.

DISCLOSURE OF THE INVENTION

Previously, aromatic liquids such as perfume have been applied directly to a person's skin in a convenient area, such as behind the ears or on the wrist, in order to produce a pleasant fragrance for a period of time. While this method of application is easy to perform and achieves the purpose, the fragrance is often short-lived as its intensity decreases with wearing and is eliminated by bathing. Additionally, some persons are allergic or at least sensitive to an aromatic liquid when it is applied directly to the skin.

Therefore, the primary object of the invention is to keep aromatic liquids from directly touching a person's skin. Application of the aromatic is accomplished by using a dropper to directly apply the aromatic liquid into a set of four openings located on one side of a fragrance chamber. When it is worn, the fragrance chamber faces away from the skin, and the aromatic liquid is absorbed into the chamber, thus releasing a fragrance from the four openings.

In addition to the primary object of the invention, it is also an object of the invention to produce a disposable pierced earring fragrance chamber that:

is more sanitary then existing fragrance devices that are refillable and that require periodic cleaning, is disposable and the aromatic liquid can be changed without refilling, thus aromatic liquids are not mixed with each other, utilizes a chamber that is hypo-allergenic since it is made of a thermoplastic that has been approved to be in direct contact with the human body, provides a fragrance chamber that is easily handled, when an aromatic liquid is applied into the chamber the fragrance lasts longer, by using the chamber, an aromatic liquid does not change on the wearer, as it does when placed directly on the skin.

when mounted onto an earring post, the post is completely protected from the aromatic liquid because of an interlocking design feature within the center of the chamber that the post slides in and out of, eliminates the chance of an aromatic liquid getting into the pierced opening of the wearer. This isolation of the aromatic liquid form the earring post is important since the post can become contaminated with the aromatic liquid.

can be used with almost any aromatic liquid including perfume, essential oils or insect repellents. This is important as the aromatic liquid never touches a person's skin, therefore any type of aromatic liquid may be used with complete confidence, utilizes a pad within the fragrance chamber that is flesh colored, and the outer casing body of the chamber is translucent with a transparent inner casing lid such that the flesh colored material of the fragrance chamber is visually obscured, thus causing the invention to be unobtrusive and to visually blend with the wearer's skin.

is so lightweight that it is hardly felt by the wearer, the chamber may be used with any type of normal pierced earring posts, can also be furnished in a kit form with a small eye dropper, extra disposable chambers, aromatic liquids and the like, unlike other fragrance diffusers, the chamber has a large flat surface that supports the ear lobe in a vertical position, when wearing large earrings, and is cost effective since it is made by injection molding. Once the tooling cost is amortized the individual piece price is minimal when produced in quantity due to the economy of numbers. The pads are likewise inexpensive to produce using multiple unit steel rule dies and conventional punch presses, thus inexpensive for the public to buy.

These and other objects and advantages of the present invention will become apparent from the subsequent detailed description of the preferred embodiment and the appended claims taken in conjunction with the accompanying drawings.

BEST MODE FOR CARRYING OUT THE INVENTION

Figure 1:
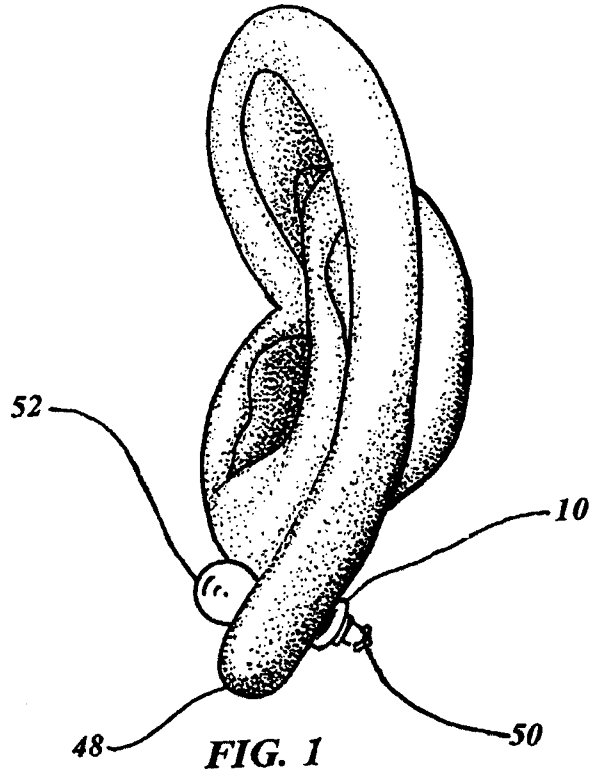
FIG. 1 is a partial isometric view of a person's ear with the fragrance chamber on the back of the ear lobe retained by the pierced earring post and held in place with a earring clasp in a first embodiment of the invention.
Figure 2:
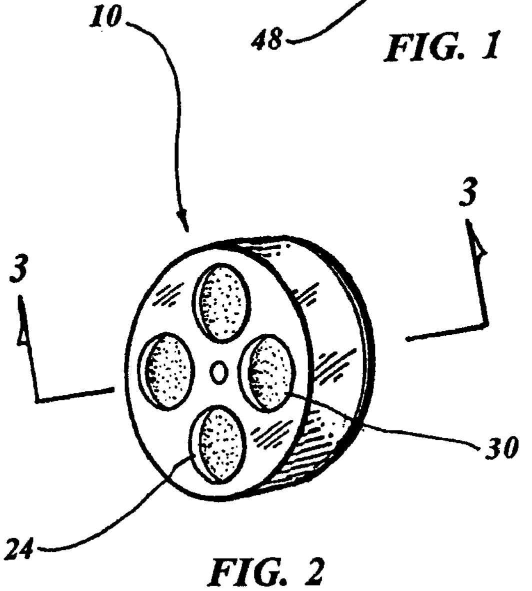
FIG. 2 is a partial isometric view of the fragrance chamber of the first embodiment.
Figure 3:
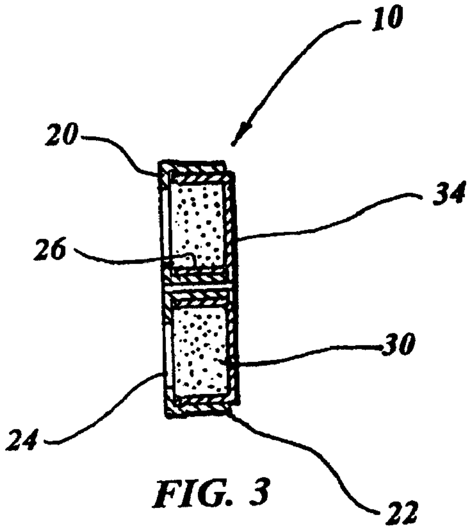
FIG. 3 is a cross-sectional view taken along line 3-3 of FIG. 2.
Figure 4:
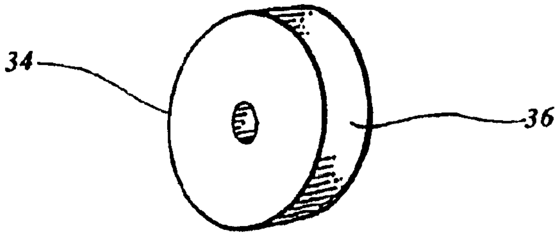
FIG. 4 is a partial isometric view of the inner casing lid of the first embodiment.
Figure 5:
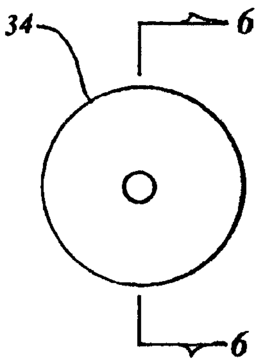
FIG. 5 is a rear view of the inner casing lid of the first embodiment.
Figure 6:
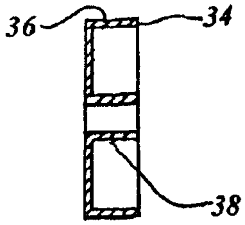
FIG. 6 is a cross-sectional view taken along line 6-6 of FIG. 5.
Figure 7:
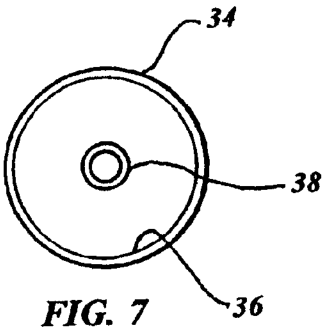
FIG. 7 is a front view of the inner casing lid of the first embodiment.
Figure 8:
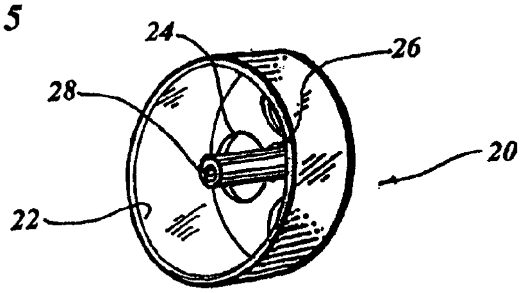
FIG. 8 is a partial isometric view of the outer casing body of the first embodiment.
Figure 9:
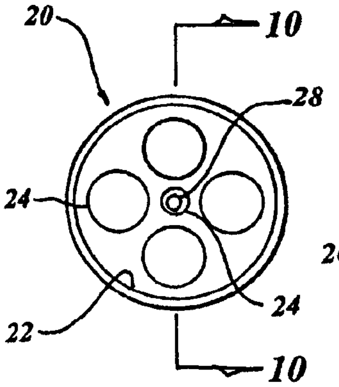
FIG. 9 is a front view of the outer casing body of the first embodiment.
Figure 10:
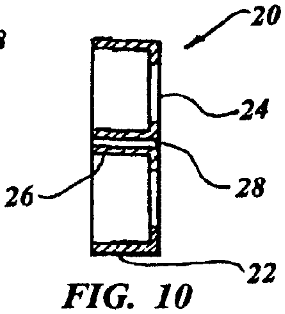
FIG. 10 is a cross-sectional view taken along line 10-10 of FIG. 9.
Figure 11:
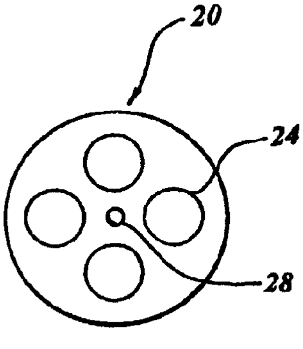
FIG. 11 is a rear view of the outer casing body of the first embodiment.

The invention is presented in terms of an embodiment for a disposable fragrance chamber 10, which is used to dispense a fragrance from behind a pierced ear lobe mounted on a pierced earring post 40 that is secured by an earring clasp 50 to which is attached an earring 52. The disposable fragrance chamber 10, as shown in FIGS. 1 through 22, is comprised of a flat dish-shaped outer casing body 20 that incorporates an outward-extended perimeter edge 22, as shown best in FIGS. 3, 8-11 and 16.

The outer casing body 20 has a plurality of pad exposure openings 24 that are arranged in a symmetrical array, and an earring post column 26 with a bore 28 therethrough in the center. The earring post column's 26 height is identical to the perimeter edge's 22 height, and the outer casing body 20 preferably has a diameter from 10 to 12 mm, with the perimeter edge 22 having a height from 2 mm to 4 mm and a bore 28 from 0.7 to 0.9 mm within the earring post column 26. The pad exposure openings 24 preferably have a diameter from 3 mm to 4 mm, with the casing body wall thickness from 0.6 mm to 0.7 mm.

Preferably, the outer casing body 20, as shown alone in FIGS. 8-11, is formed of a transparent resilient thermoplastic such as cellulose acetate, chlorinated polyether, ethylene vinyl acetate, nylon, polycarbonate, polyethylene, polypropylene, vinyl or polyester.

An absorbent pad 30, having a central thru-hole 32, is disposed inside the outer casing body 20 within the perimeter edge 22, with the earring post column 26 penetrating the thru-hole 32, as shown in FIGS. 2, 3 and 12-16. The absorbent pad 30 preferably has an outside diameter from 8.8 mm to 10.6 mm, a height from 1.4 mm to 3.3 mm and a thru-hole 32 diameter from 3 mm to 4 mm.

Figure 12:
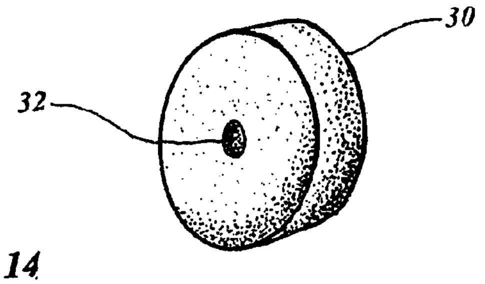
FIG. 12 is a partial isometric view of the absorbent pad of the preferred embodiment shown removed from the invention for clarity.
Figure 13:
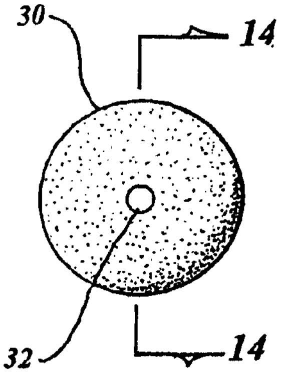
FIG. 13 is a rear view of the absorbent pad of the first embodiment.
Figure 14:
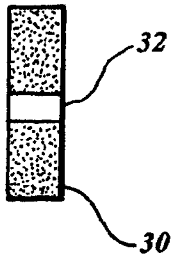
FIG. 14 is a cross-sectional view taken along line 14-14 of FIG. 13.
Figure 15:
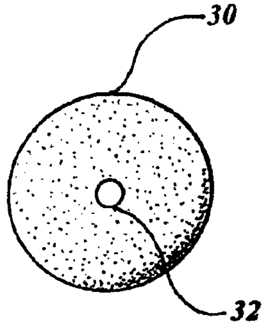
FIG. 15 is a front view of the absorbent pad of the first embodiment.
Figure 16:
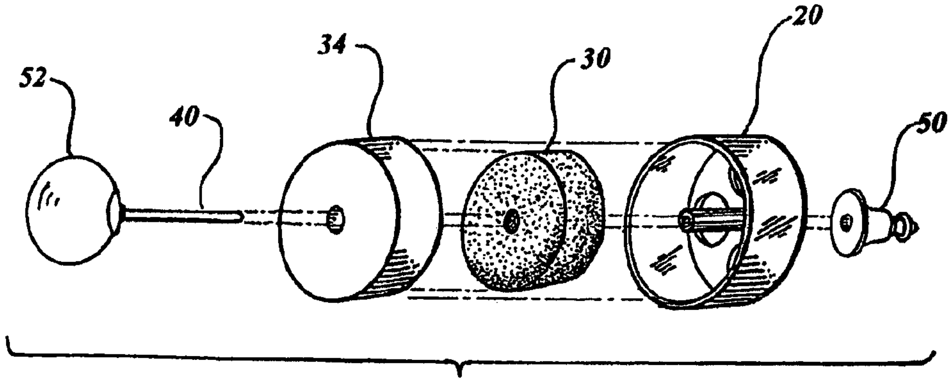
FIG. 16 is an exploded view of the pierced earring fragrance chamber in the first embodiment including an earring and clasp.

The absorbent pad 30 utilizes cotton felt as a preferred material, however other types of absorbent substances, such as open cell sponge or the like, may be used with equal ease. In order to be as concealed and non-obtrusive as possible, the absorbent pad 30 may be made using a flesh colored material. The absorbent pad 30, as shown completely removed from the invention in FIGS. 12-14, is made with conventional die-cut tooling.

A flat, dish-shape inner casing lid 34, as shown in FIGS. 4-7, includes an extended perimeter lip 36 and an earring post column sleeve 38. The inner casing lid 34 is positioned inside the outer casing body 20 and contiguously engages its perimeter edge 22 of the outer casing body 20, with the lid perimeter lip 36. The earring post column 26 also interfaces with on the column sleeve 38, thereby frictionally maintaining the lid 34 on the body 20. The disposable fragrance chamber 10 is designed to allow an aromatic liquid to be introduced into the absorbent pad 30 through the pad exposure openings 24. Once the disposable fragrance chamber 10 is installed on a conventional earring post 40 between a person's ear lobe 48 and a conventional earring clasp 50, and after the pad 30 has been moistened with the aromatic liquid, a fragrance will then be released from the liquid into the surrounding environment.

The earring post column sleeve's 38 height is identical to the perimeter lip 36 height such that the sleeve 38 engages the outer casing body 20 when assembled together. The inner casing lid preferably has a diameter from 8.8 to 10.6 mm, with the perimeter lip having a height from 1.4 mm to 3.3 mm, and the earring post sleeve 38 having a diameter from 3 to 4 mm.

The inner casing lid 34 in the preferred embodiment is made of a translucent resilient thermoplastic. The thermoplastic may be cellulose acetate, chlorinated polyether, ethylene vinyl acetate, nylon, polycarbonate, polyethylene, polypropylene, vinyl or polyester.

The fragrance chamber outer casing body 20 and inner casing lid 34 mate together with press fit or with sufficient resistance to remain attached together when assembled. The absorbent pad thru-hole 32 is sized to interface intimately with the inner casing lid 34 and the earring post column sleeve 38, while allowing sufficient clearance for the pad 30.

While any aromatic liquid introduced into the absorbent pad 30 through the pad exposure openings 24 may be used, the preferred aromatic liquids are perfumes, essential oils, and insect repellents.

Figure 17:
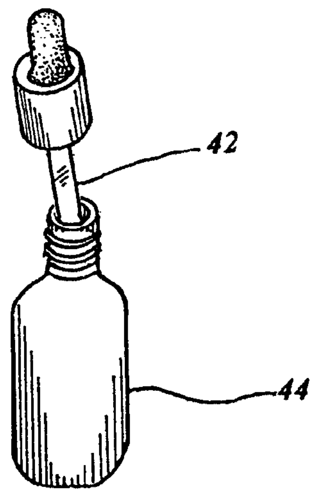
FIG. 17 is a partial isometric view of the step of filling the eye dropper from a bottle of liquid fragrance.
Figure 18:
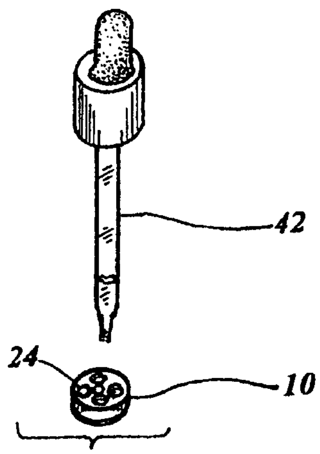
FIG. 18 is partial isometric view of the step of placing the liquid fragrance into the absorbent pad exposure openings of the chamber.
Figure 19:
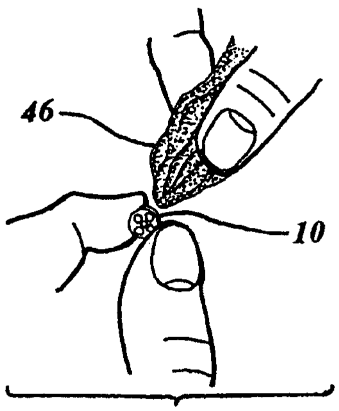
FIG. 19 is partial isometric view of the step of wiping excess liquid fragrance from the chamber.
Figure 20:
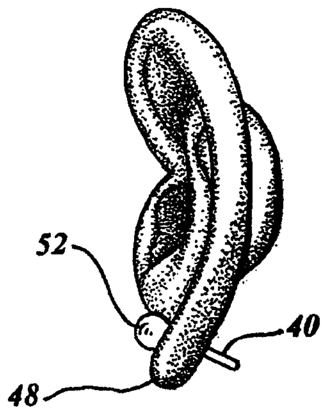
FIG. 20 is partial isometric view of the step of placing an earring post through a person's ear lobe.
Figure 21:
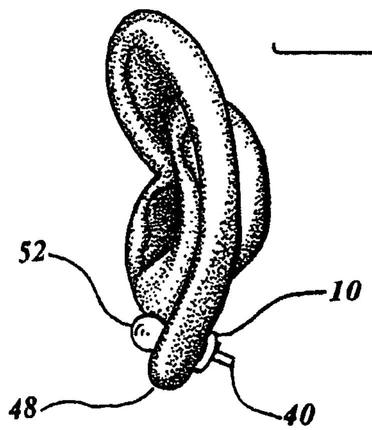
FIG. 21 is partial isometric view of the step of placing the fragrance chamber on the post extending beyond the person's ear lobe.
Figure 22:
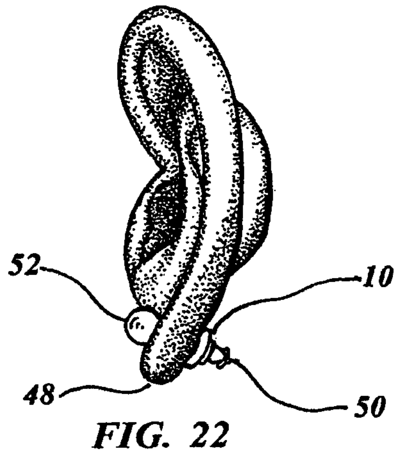
FIG. 22 is partial isometric view of the step of securing the fragrance chamber with a clasp on the earring post.

During use, the process of dispensing a fragrance from the assembled chamber 10 comprises the following steps:

a) filling a dropper 42, such as a conventional eye dropper, with an aromatic liquid from a container 44, as shown in FIG. 17, b) applying the aromatic liquid from the dropper 42 into the absorbent pad 30 through a set of pad exposure openings 24 located on the chamber 10, as shown in FIG. 18, c) wiping excess liquid if any, from the chamber with a disposable tissue 46, or the like, as shown in FIG. 19, d) placing the earring post 40 through a person's ear lobe 48, as shown in FIG. 20, e) placing the chamber 10 on the earring post 40 that extends beyond the ear lobe 48, as shown in FIG. 21, and f) securing the chamber 10 with an earring clasp 50, as shown in FIG. 22, thereby permitting a fragrance to be emitted from the aromatic liquid into a surrounding environment.

Figure 23:
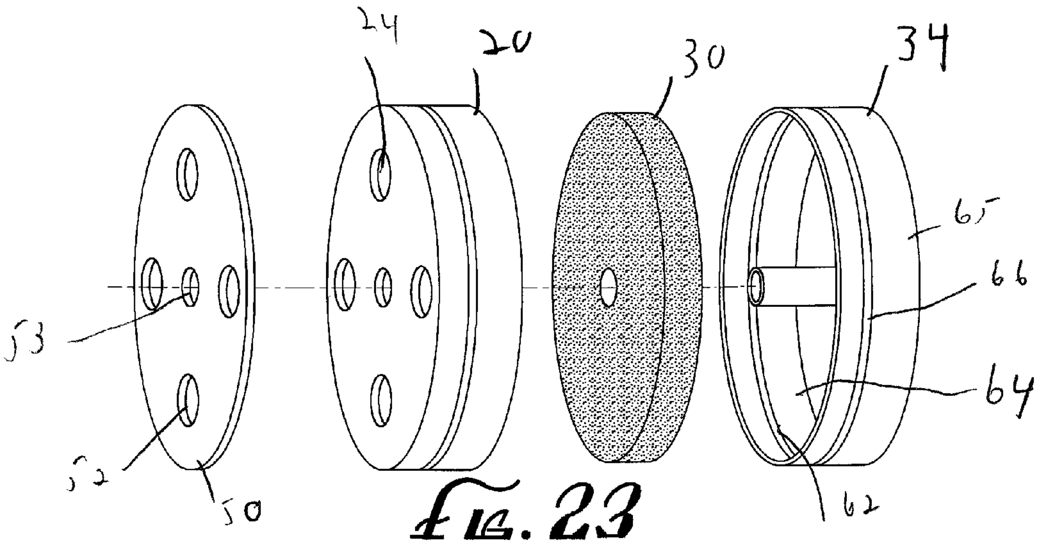
FIG. 23 is an exploded view of a second version of the invention having a first closure member.
Figure 24A:
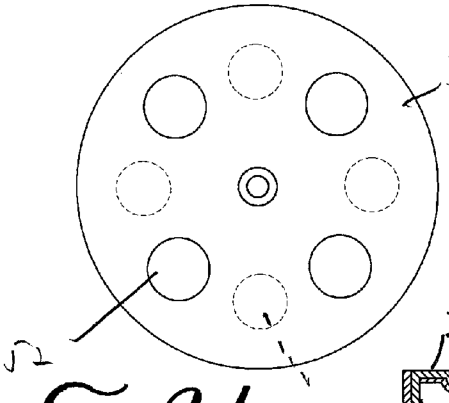
FIGS. 24A and 24B are front plan views of the second version of the invention in a closed position and open position, respectively.
Figure 24B:
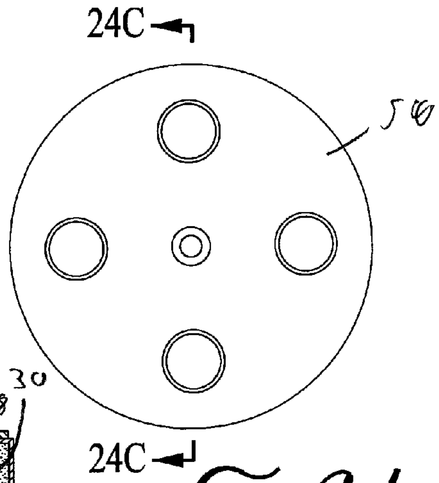

With reference to FIGS. 23 and 24A-C, this second version of the invention has three features that are not present in the versions previously discussed. In particular, a cover plate, also referred to as a cover member 50, mounted on and movable relative to the outer casing body 20, is used for closing or covering the pad exposure openings 24. The cover member 50 can be a solid plate that can be removably placed over the openings 24 such as by a snap fit. Alternatively and preferably, to avoid losing the cover member 50. It is rotatably mounted on the outer casing body 20, and has a plurality of openings 52 that match up with the corresponding pad exposure openings 24 in an "open" position as shown in FIG. 24B. By moving the cover member 50 relative to the outer casing body 20 such as by rotation, the pad exposure openings 24 are covered, as shown in FIG. 24A. This feature preserves the fragrance, adding to the life of the device. The cover member 50 has a central opening 53 that is aligned with the corresponding openings of the other elements of the chamber for receiving the earring post 40. Although the closure member is shown in FIG. 24A (?) as completely closing the openings 24, it is possible to only partially close the openings 24, thereby controlling the rate at which a fragrance is dispersed.

Figure 24C:
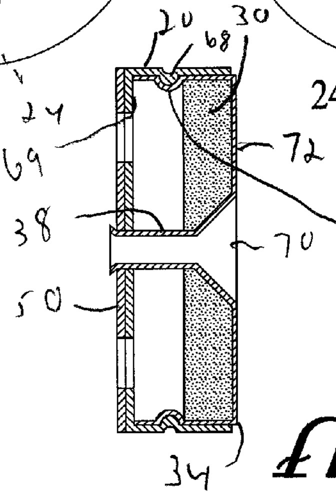
FIG. 24C is a sectional view of the second version of the invention assembled, taken along line 24A-24C in FIG. 24B.
Figure 25:
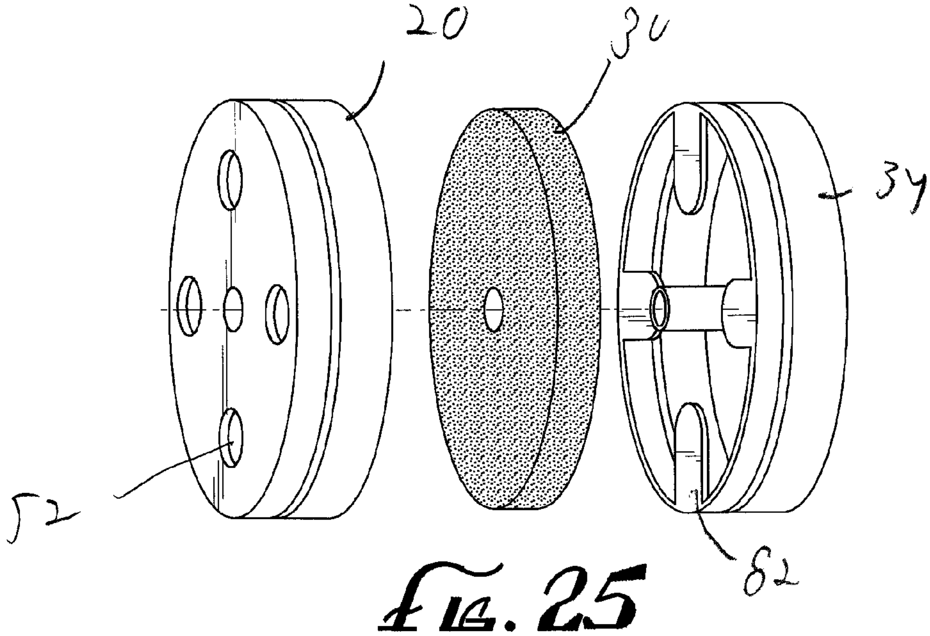
FIG. 25 is an exploded view of a third version of the invention having a second closure member.

The second feature is an inner circumferential ridge or rib 62 on the inside surface 64 of the inner casing lid 34. This ridge 62 prevents liquid fragrance from leaking out of the chamber. Preferably the outer surface 65 of the lid 34 has a corresponding circumferential détente 66 for receiving a mating ridge 68 on the inside surface 69 of the casing body 20, as best shown in FIG. 24C. This helps retain the casing body 20 and casing lid 34 together. The ridge 62 avoids the problem of seepage of fragrance from over-saturated pads, which can result when a manufacturer or consumer dispenses too much liquid fragrance into the pad 30. Also, even when the proper quantity of aromatic fragrance is used, gravity can cause liquids to flow towards the bottom portion of the device, thereby increasing the possibility of leakage.

Figure 26A:
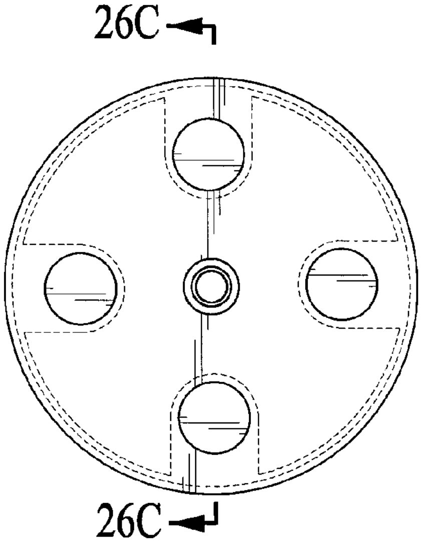
FIGS. 26A and 26B are front plan views of the third version of the invention in a closed position and open position, respectively.
Figure 26B:
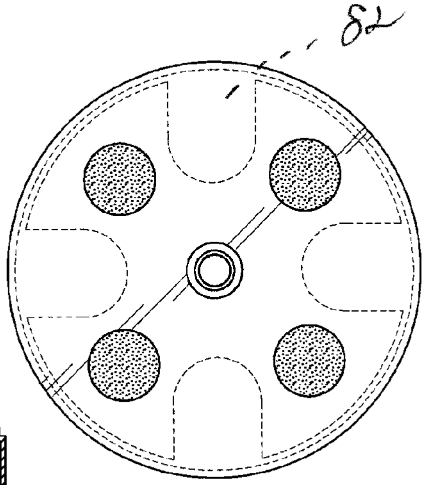
Figure 26C:
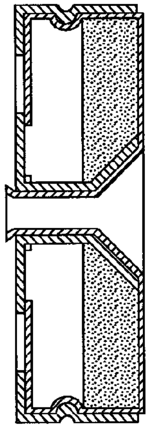
FIG. 26 is a sectional view of the third version of the invention assembled, taken along line 26A-26C in FIG. 26B.

A third feature of the version of the invention shown in FIGS. 24C and 26C is an enlargement of the earring post receiving opening 70 in the outer surface 72 of the lid 34. The opening 70 is tapered to have a larger outer surface, reducing in size to match that of the bore of the earring post column sleeve 38. This makes it easier for a user to thread the fragrance chamber into an earring post. By the term "tapered," there is meant a gradual diminution of diameter. This need not be accomplished with smooth constant diminution; it is possible for adjoining segments of the opening to be of the same in diameter. The taper can be at a 45° angle, tapering down to an aperture slightly smaller, by about 3 mils, than the earring post diameter. Earring posts are typically about 0.7 to about 0.8 mm, and more typically about 0.73 mm, in diameter.

The version of the invention shown in FIGS. 25 and 26A-C is substantially the same as the version of the invention shown in FIG. 23. It differs in that a separate closure member is not used. Instead the casing bodies are rotatable relative to each other, and the casing body not having the pad exposure opening comprises projections for at least partially blocking at least one pad exposure opening, and preferably all the pad exposure openings, in a closed position. In an open position, the projections, which are preferably tabs, unblock the pad exposure openings. In particular, with reference to FIGS. 25 and 26A-C, the inner casing lid 34 has inwardly projecting blocking elements such as tabs 82. The lid 34 is rotatable relative to the body 20. By rotating the lid 34, the tabs 82 can block the pad exposure openings 52 in a closed position as shown in FIG. 26A, or can expose the openings 52 in an open position, as shown in FIG. 26B.

While the invention has been described in detail and pictorially shown in the accompanying drawings, it is not to be limited to such details, since many changes and modifications may be made to the invention without departing from the spirit and scope thereof. Hence, it is described to cover any and all modifications and forms which may come within the language and scope of the appended claims.

The invention claimed is:

1. A chamber for use in combination with an earring having a post for penetrating a person's ear lobe and a clasp, wherein the chamber is sized to fit on the post between the clasp and the person's ear lobe, the chamber comprising:

a) a housing having opposed first and second surfaces, the first surface for facing the person's ear lobe and the second surface for facing the clasp, the housing being sized and configured to fit on the post between the clasp and the person's ear lobe;

b) a plurality of pad exposure openings in the second surface with no pad exposure openings in the first surface;

c) a first earring post receiving opening in the first surface and a second earring post receiving opening in the second surface for receiving the earring post; and d) an absorbent pad within the housing for receiving an aromatic liquid or having absorbed aromatic liquid, wherein the housing comprises (A) a flat, dish-shape inner casing lid comprising (i) the first surface; (ii) an extended perimeter lip, and (iii) a first earring post column having a bore therethrough, the first earring post receiving opening being in communication with the first earring column bore; and (B) a flat, dish-shaped outer casing body comprising (i) an outward-extended perimeter edge, (ii) the second surface and the pad exposure openings, and (iii) a second earring post column having a bore therethrough, wherein the inner casing lid is positioned inside the outer casing body contiguously engaging the perimeter edge with the second earring post column being within the first earring post column.

2. The chamber of claim 1 wherein the outer casing body has an inner circumferential ridge.

3. The chamber of claim 1 comprising an inner circumferential ridge.

4. The chamber of claim 1 wherein the housing is formed of a transparent plastic and the absorbent pad is flesh colored.

5. The chamber of claim 1 wherein the absorbent pad opening interfaces intimately with the first earring post column.

6. The chamber of claim 1 wherein the outer casing body and the inner casing lid mate together with a press fit.

7. The chamber of claim 1 wherein the aromatic liquid is selected from the group consisting of perfumes, essential oils, and insect repellents.

8. A process for a person to apply an aromatic liquid without aromatic liquid fragrance contacting the person comprising the steps of:

a) selecting the chamber of claim 1;

b) if the pad does not have an aromatic liquid, applying an aromatic liquid to the pad through the pad exposure openings;

c) placing the chamber on an earring post penetrating the person's ear, with the pad exposure openings facing away from the ear lobe; and d) after step c), placing a clasp on the earring post.

9. The process of claim 8 wherein the pad does not have an aromatic liquid, and in step (b) aromatic liquid is applied to the pad through the pad exposure openings.

10. The chamber of claim 1 comprising a movable cover for covering the pad exposure openings.

11. The chamber of claim 10 wherein the movable cover is rotatable and has openings for aligning with pad exposure openings in an open position and covers the pad exposure openings in a closed position.

12. The chamber of claim 1 wherein the casing body and the casing lid are rotatable relative to each other, and the housing comprises projections for at least partially blocking at least one pad exposure opening in a closed position, and for unblocking the pad exposure openings in an open position.

13. The chamber of claim 1 wherein the earring post columns protect the earring post form the aromatic liquid and, wherein the absorbent pad has an opening through which the earring post columns extend.

14. The chamber of claim 13 wherein the first earring post receiving opening is tapered to be larger at the first surface than at the earring post column bore for ease in mounting the chamber on the earring post.

15. A fragrance system comprising an earring having a post penetrating a person's ear lobe, the chamber of claim 1 on the post between the ear lobe and the person's head, the pad having an absorbed aromatic liquid, and the clasp on the post farther from the ear lobe than is the chamber.

16. The chamber of claim 1 wherein the earring post receiving opening is tapered to be larger at the first surface than at the first earring post column for ease in mounting the chamber on the earring post.

17. The chamber of claim 1 wherein the absorbent pad has an opening through which the columns extend.

18. The chamber of claim 1 wherein the earring post columns are centrally located and aligned such that one column slides over the other earring post column with a slip fit when the first and second casing bodies are assembled together.

19. A chamber for use in combination with an earring having a post for penetrating a person's ear lobe and a clasp, wherein the chamber is sized to fit on the post between the clasp and the person's ear lobe, the chamber comprising:

a) a housing having opposed first and second surfaces, the first surface for facing the person's ear lobe and the second surface for facing the clasp;

b) a plurality of pad exposure openings in the second surface with no pad exposure openings in the first surface, c) a first earring post column through the housing and having a bore through the column for receiving the post;

d) a first post receiving opening in the first surface and in communication with the first earring post column bore for receiving the earring post and a second post receiving opening in the second surface for receiving the earring post; and e) an absorbent pad within the casing body for receiving an aromatic liquid or having an absorbed aromatic liquid, the pad having an opening through which the first earring post column extends;

wherein the housing comprises (A) a flat, dish-shape inner casing lid comprising (i) the first surface; (ii) an extended perimeter lip, and (iii) the first earring post column having a bore therethrough, wherein the first earring post receiving opening is in the first surface; and (B) a flat, dish-shaped outer casing body comprising (i) an outward-extended perimeter edge, (ii) the second surface and the pad exposure openings, and (iii) a second earring post column having a bore therethrough, wherein the inner casing lid is positioned inside the outer casing body contiguously engaging the perimeter edge with the second earring post column being within the first earring post column.

20. The chamber of claim 19 wherein the first post receiving opening is tapered to be larger at the first surface than at the earring post column bore for ease in mounting the chamber on the earring post.

21. The chamber of claim 19 comprising an inner circumferential ridge.

22. The chamber of claim 19 wherein the housing is formed of a transparent plastic and the absorbent pad is flesh colored.

23. The chamber of claim 19 comprising a movable cover for covering the pad exposure openings.

24. The chamber of claim 23 wherein the movable cover is rotatable and has openings for aligning with pad exposure openings in an open position and covers the pad exposure openings in a closed position.

* * * * *